United States Patent [19]
Fuchs et al.

[11] Patent Number: 6,153,748
[45] Date of Patent: Nov. 28, 2000

[54] METHOD FOR HYDROGENATING COMPOUNDS FROM THE GROUP OF IMINES OR ENAMINES

[75] Inventors: Eberhard Fuchs, Frankenthal; Frank Ohlbach, Dörsdorf, both of Germany

[73] Assignee: BASF Aktiengesellschaft, Ludwigshafen, Germany

[21] Appl. No.: 09/367,069

[22] PCT Filed: Jan. 26, 1998

[86] PCT No.: PCT/EP98/00414

§ 371 Date: Aug. 9, 1999

§ 102(e) Date: Aug. 9, 1999

[87] PCT Pub. No.: WO98/34899

PCT Pub. Date: Aug. 13, 1998

[30] Foreign Application Priority Data

Feb. 7, 1997 [DE] Germany ............... 197 04 615

[51] Int. Cl.$^7$ ............... C07D 223/02; C07C 253/34; C07C 255/24
[52] U.S. Cl. ............... 540/484; 502/66; 502/167; 564/448; 564/461
[58] Field of Search ............... 564/448, 461; 540/484; 502/66, 167

[56] References Cited

U.S. PATENT DOCUMENTS

| | | | |
|---|---|---|---|
| 5,527,946 | 6/1996 | Flick et al. | 558/459 |
| 5,679,860 | 10/1997 | Haas et al. | 564/448 |

FOREIGN PATENT DOCUMENTS

| | | |
|---|---|---|
| 497333 | 8/1992 | European Pat. Off. . |
| 502439 | 9/1992 | European Pat. Off. . |
| 195 40191 | 10/1995 | Germany . |
| 196 30 788 | 7/1996 | Germany . |
| 196 36 765 | 3/1998 | Germany . |
| 196 36 768 | 3/1998 | Germany . |
| 196 46 436 | 5/1998 | Germany . |
| 96/20166 | 7/1996 | WIPO . |

*Primary Examiner*—Mukund J. Shah
*Assistant Examiner*—Pavanaram K Sripada
*Attorney, Agent, or Firm*—Keil & Weinkauf

[57] ABSTRACT

A process for hydrogenating a compound in the group of the imines or enamines I to an amine II in the presence of a nitrile III, said nitrile III being essentially not hydrogenated comprises reacting a mixture comprising a compound I and a nitrile III with a gas comprising molecular hydrogen in the presence of a catalyst IV.

4 Claims, No Drawings

METHOD FOR HYDROGENATING COMPOUNDS FROM THE GROUP OF IMINES OR ENAMINES

This Application is a 371 of PCT/EP98/00414 filed Jan. 26, 1998.

DESCRIPTION

The present invention relates to a process for hydrogenating a compound in the group of the imines or enamines I to an amine II in the presence of a nitrile III, said nitrile III being essentially not hydrogenated, which comprises reacting a mixture comprising a compound I and a nitrile III with a gas comprising molecular hydrogen in the presence of a catalyst IV.

The present invention further relates to the use of catalysts for converting imines or enamines into amines in the presence of nitriles, the nitriles being essentially not hydrogenated, using a gas comprising molecular hydrogen.

Processes for hydrogenating imines or enamines in the presence of nitriles essentially without hydrogenating the nitriles are known.

EP-A-0 502 439 discloses reacting an imine such as tetrahydroazepine with an appreciable excess of hydrides such as sodium borohydride or lithium tri-tert-butoxyaluminum hydride in the presence of a nitrile such as 6-aminocapronitrile to form N-(5-cyanopentyl)-1,6-hexamethylenediamine. Disadvantageously, in this process, the hydride is used in four- to fivefold excess and, after the reaction, the salt formed from the hydride has to be separated off. In addition, the post-hydrogenation process used for working up the product mixture has to be adapted specifically to the remaining hydride and all the products in order that a hydrogenation of the nitrile may be avoided during workup.

It is an object of the present invention to provide a process which is free of the disadvantages mentioned and which makes it possible to hydrogenate imines to amines in the presence of nitriles in a technically simple and economical manner essentially without hydrogenating the nitriles.

We have found that this object is achieved by the process mentioned at the beginning and by the use of catalysts therefor.

Compound I is preferably a cyclic imine, for example 3,4,5,6-tetrahydroazepine, or a cyclic enamine, for example 4,5,6,7-tetrahydroazepine, or a mixture thereof.

Such imines and enamines and also processes for their preparation are generally known.

These imines or enamines can be present as individual compounds or as adducts, especially with amines, in which case these adducts shall herein likewise be referred to as imines or enamines.

Tetrahydroazepine can be obtained in the partial catalytic hydrogenation, using a gas comprising molecular hydrogen, of adiponitrile to 6-aminocapronitrile or mixtures comprising 6-aminocapronitrile and hexamethylenediamine, generally in amounts from 10 ppm to 5% by weight based on 6-aminocapronitrile.

The catalysts which can be used in this hydrogenation are advantageously those based on a metal selected from the group consisting of rhodium, nickel, cobalt, preferably iron, in which case the catalysts may include further elements as promoters. In the case of catalysts based on iron, suitable promoters are in particular one or more, such as two, three, four or five, elements selected from the group consisting of aluminum, silicon, zirconium, titanium and vanadium.

Such catalysts and also the process conditions for the reaction mentioned are described for example in WO-A-96/20166, German Application 19 636 768.9 and German Application 19 646 436.6.

Adiponitrile, aminocapronitrile and hexamethylenediamine, from each of which tetrahydroazepine is not simple to separate, are major fiber intermediates for the production of polyamides such as nylon-6 or nylon-6,6, in each of which tetrahydroazepine is customarily present as an undesirable, color-conferring compound.

Suitable nitriles III are preferably acyclic nitriles, for example adiponitrile and 6-aminocapronitrile, and also mixtures thereof.

Suitable amines V are preferably acyclic amines, especially hexamethylenediamine and 6-aminocapronitrile, and also mixtures thereof, and the amine V preferably differs from the amine II.

The preparation of such amines can be effected in a conventional manner, for example by the processes mentioned for the preparation of tetrahydroazepine.

Suitable catalysts are preferably those based on noble metals, especially palladium and platinum and also their mixtures. The catalysts can be doped with cobalt, iron, nickel, rhodium, ruthenium or mixtures thereof, preferably in amounts from 0.1 to 15% by weight based on the total amount of catalytically active elements.

The catalysts can be used with advantage in the form of supported catalysts, commendable support materials being aluminum oxide, silicon oxide, titanium oxide, zirconium oxide and mixtures thereof, especially activated carbon. The catalyst supports can be doped with compounds of the alkali metals and alkaline earth metals or mixtures thereof.

Such catalysts are known per se.

The reaction is carried out in the gas phase or preferably in the liquid phase continuously over a fixed bed catalyst, especially in the presence of from 0.01 to 2% by weight of water, based on the sum of nitrile III and compound I. The reaction temperature is within the range from 20 to 150° C., preferably within the range from 40 to 120° C. The gas phase reaction is carried out at a pressure such that the amine/nitrile mixture to be purified is present in the gas phase together with hydrogen. In the liquid phase, the pressure should be within the range from 1 to 200 bar, preferably within the range from 5 to 80 bar. Hydrogen is added pure or diluted with 5–95% of nitrogen at the corresponding pressure.

The amine II can be removed from the reaction mixture according to conventional processes, for example by distillation or extraction. Such processes are described in German Application 19 636 765.4, for example.

If tetrahydroazepine is used as imine I and 6-aminocapronitrile as nitrile III, the process of the invention affords azepan as amine II in the presence or absence of hexamethylenediamine as amine V. Azepan is readily removable from 6-aminocapronitrile and any hexamethylenediamine, so that the process of the invention can be used to obtain fiber intermediates of high purity and fibers of good color stability.

What is claimed is:

1. A process for hydrogenating a tetrahydroazepine to an amine in the presence of 6-aminocapronitrile comprising reacting gaseous molecular hydrogen with said tetrahydroazepine and 6-aminocapronitrile in the presence of a noble metal hydrogenation catalyst, the nitrile being essentially not hydrogenated.

2. The process of claim 1, wherein the hydrogenation is carried out in the presence of hexamethylenediamine.

3. The process of claim 1, wherein the catalyst contains palladium or platinum as catalytically active component.

4. The process of claim 1, wherein the catalyst is a supported catalyst.

* * * * *